(12) United States Patent
Gdula

(10) Patent No.: US 11,717,249 B2
(45) Date of Patent: Aug. 8, 2023

(54) IMAGE CAPTURE METHOD AND APPARATUS

(71) Applicant: Steven A. Gdula, Crystal Lake, IL (US)

(72) Inventor: Steven A. Gdula, Crystal Lake, IL (US)

( * ) Notice: Subject to any disclaimer, the term of this patent is extended or adjusted under 35 U.S.C. 154(b) by 22 days.

(21) Appl. No.: 17/578,888

(22) Filed: Jan. 19, 2022

(65) Prior Publication Data

US 2022/0133256 A1 May 5, 2022

Related U.S. Application Data

(63) Continuation of application No. 16/868,614, filed on May 7, 2020, now Pat. No. 11,259,769.

(51) Int. Cl.
*A61B 6/00* (2006.01)
*G21K 1/04* (2006.01)
*G21K 1/10* (2006.01)
*A61B 6/06* (2006.01)
*G21K 1/02* (2006.01)

(52) U.S. Cl.
CPC .............. *A61B 6/5241* (2013.01); *A61B 6/06* (2013.01); *A61B 6/4452* (2013.01); *G21K 1/02* (2013.01); *G21K 1/10* (2013.01)

(58) Field of Classification Search
CPC ......... A61B 6/06; A61B 6/542; A61B 6/5421; A61B 6/544; A61B 6/032; A61B 6/4035; A61B 6/035; A61B 6/025; G21K 1/04; G21K 1/02; G21K 1/046; G21K 1/043; G21K 5/04; G21K 5/10; G21K 1/08; A61N 5/1045; A61N 5/1042
See application file for complete search history.

(56) References Cited

U.S. PATENT DOCUMENTS

| | | |
|---|---|---|
| 4,489,426 A | 12/1984 | Grass et al. |
| 5,296,534 A | 3/1994 | Senuma |
| 2021/0190705 A1* | 6/2021 | May ..................... G01N 23/083 |

* cited by examiner

*Primary Examiner* — Don K Wong
(74) *Attorney, Agent, or Firm* — Aronberg Goldgehn Davis & Garmisa

(57) ABSTRACT

The present apparatus, system, and method relate to reliably capturing multiple x-ray images for later combination. An exposure shield blocks a portion of the x-rays emitted from a traditional emitter and collimator. The orientation of exposure shield may then be modified to block a second portion of x-rays while ensuring appropriate overlap of the captured images without intentionally moving the emitter or collimator and without the need for a patient to wear protective garb.

11 Claims, 10 Drawing Sheets

IMAGE CAPTURE METHOD AND APPARATUS

CROSS REFERENCE

This application claims priority to and incorporates herein by this reference in its entirety and for all purposes U.S. patent application Ser. No. 16/868,614 filed on behalf of Steven A Gdula on May 7, 2020.

BACKGROUND

X-ray imaging systems are often used as a means of imaging subcutaneous structures, and particularly bones of human or animal subjects. The problem is that overexposure to radiation, such as x-rays, can be dangerous. Therefore, subjects must shroud themselves in protective gear, such as a lead apron, or the x-ray radiation must be limited at the source to the clinical region of interest so as to only to expose a minimal amount of tissue when undergoing x-ray imaging. Additionally, subjects must remain still thought the imaging process.

Sometimes a larger area of the subject must be imaged in a manner that cannot be accomplished in a single x-ray exposure. For example, imaging a spinal column generally requires that the x-ray emitter project multiple doses of x-rays various angles or positions while a detector behind the patient is moved after each dose projection. The process is accomplished in stages such that a first image is taken, the radiation emitter and radiation detector are moved, a second image is taken, and the emitter and detector are moved again before another image is taken. The process repeats until the full area is captured. A technician must then review the images and attempt to align the images and stitch them together to form a single cohesive x-ray image of the patient.

During the process, to avoid over exposure to radiation, two options are available. One option is to maximize the projection field of radiation from the emitter. However, in that case, the patient must cover a portion of their body with lead to prevent unnecessary damage to areas of the body that cannot be captured during the exposure due to the size of the detector or that are not needed to be captured for the x-ray procedure. The lead shielding must then be moved along with the detector for the second image and the process must be repeated for additional images. The process requires movement of the lead shielding which can cause the subject to move and may require movement of the detector as well. Either movement increases the overall patient hold time considerably and risks misaligning the patient such that stitching of multiple x-rays cannot be accomplished.

Alternately, to avoid cumbersome shielding, the radiologic technologist must adjust the x-ray system, such as through the use of a collimator, to expose only the clinical region of interest before every exposure. However, for each exposure, the technician must readjust the position of the x-ray emitter and the scope of the collimator to account for the new region of interest, thereby causing the patient hold time to increase to several minutes. In that adjustment period, it is often the case that a subject will move, and such movement has a detrimental effect on the quality of the x-ray as successive x-ray images will not perfectly align and thereby prevent stitching. The movement of the x-ray emitter presents similar problems to patient movement. It takes time and, if the technician does not capture sufficient overlap between images, the successive images cannot be properly stitched.

In either case, the process is time consuming as the x-ray technician must align and reset the x-ray emitter and detector multiple times while attempting to minimize movement of the subject. While large x-ray detectors can be purchased to acquire the entire image at one time, or fully robotic and automated systems could be used, such machines are, for many, prohibitively expensive or too large for the needs or available space of a practitioner.

There is a need in the field to accurately capture successive x-ray images using a single small-format x-ray detector while limiting the dose of x-ray radiation experienced by the subject, limiting the time required to capture multiple exposures, limiting the patient's hold time to prevent movement of the patient between multiple exposures and maintain the position of the x-ray emitter and collimator for each x-ray image capture and allowing for capture of multiple x-ray images that can readily and reliably be stitched together to create a single x-ray image.

SUMMARY

Throughout the specification, wherever practicable, like structures will be identified by like reference numbers. In some figures, components, such as additional electrical connections or fasteners have been omitted for clarity in the drawings. Unless expressly stated otherwise, the term "or" means "either or both" such that "A or B" includes A alone, B alone, and both A and B together.

The present apparatus and system provides the ability to reliably capture multiple x-ray images without the need to reposition the x-ray emitter or adjust the collimator while minimizing the dose of radiation experienced by the subject. One part of the system blocks a portion of the x-rays at the emitter when a first image is taken. Another part of the system allows the detector to be reliably moved in a consistent manner, such that a subsequent x-ray image will reliably stitch to the initial image. The blocking system may be altered to block different portion of x-rays while the subsequent image is captured all without intentionally moving the emitter, collimator, or subject and can capture multiple x-ray images while exposing the subject to the minimum necessary dose of radiation but without the need for the patient to utilize protective covering (for example, a lead apron).

The system includes an x-ray generator within a housing and a beam limiting device, hereinafter referred to as a collimator, to control the size and shape of the field of emitted x-rays (the field may alternatively be referred to as the x-ray beam). The housing substantially blocks x-ray radiation while the collimator provides an outlet path for the emission of x-rays and allows a technician to narrow or widen the x-ray beam and for the emission of x-rays from housing. The collimator may include a proximal end that is located proximal to the source of the x-ray generator and a distal end separated from the proximal end. The distal end may include an aperture providing a point for the x-rays to egress from the housing and be emitted toward a target. The distal end of the collimator may include one or more brackets (or, pins, clips, grips, detents, etc.). The brackets may be adapted to retain an exposure shield. The positioning of the brackets may be matched with the configuration of the exposure shield such that the exposure shield may engage the brackets so as to be held in place by the brackets in proper alignment of the exposure shield over the distal end of the collimator.

In one embodiment, when engaged with the brackets in a first position, the exposure shield blocks a first portion of the x-ray beam that would otherwise be emitted from the distal end of the collimator in the absence of the exposure shield. The exposure shield blocks a second, and different portion of the x-ray beam when engaged in a second position. In that way, the exposure shield may be placed in a first position, the emitter may be activated to emit x-rays, some of which are blocked by the exposure shield while another portion of the x-rays are not blocked and instead are allowed to penetrate the patient and form an x-ray image on the detector. The detector may then be moved, the exposure shield may be engaged in a second position, and emitter may be activated a second time such that a different portion of x-rays are blocked, and a different portion of x-rays are allowed to penetrate the patient and form an x-ray image on the detector. In that way, multiple different images may be acquired while minimizing a subject's exposure to x-rays and the collimator does not require focusing adjustments and both the emitter and the patient remain stationary. In general, for a two exposure capture, the present system may reduce patient hold times from 45 seconds or more per exposure to 15 seconds or less per exposure.

The exposure shield may be paired with a detector to form a further embodiment of the present system. The system includes a cabinet housing a movable detector. The cabinet includes a front face and a cavity behind the front face. The cavity accommodates a movable x-ray detector. The cabinet may further include guides, such as rails, adapted to guide the movement of the detector within cabinet. The detector or cabinet also includes one or more retention locks that lock the detector in various positions. Thus the detector may be locked in a first position at the top portion of the cabinet. The retention lock may be disengaged and the detector may be guided along the guides to a second position where the retention lock is reengaged to hold the detector in the second position. The cabinet may further include one or more cabinet mounting brackets that may be affixed to a wall or other structural surface or to a mounting arm or cart. In any case, the mounted cabinet may be held in place such that the cabinet remains stationary while the detector moves within the cabinet.

The lock(s) utilized for retaining the detector within the cabinet may be positioned such that when the lock is engaged in a first position, the position of the detector corresponds to the exposure field of the x-rays when the exposure shield is in the first position. And, when the lock is engaged in a second position, the position of the detector corresponds to the exposure field of the x-rays when the exposure shield is in the second position. The position of the lock(s) further ensure that there is sufficient overlap on the detector between the first and second positions that the images captured in the first and second exposures will stitch together.

Using both the cabinet and the exposure shield together, a technician may easily and reliably capture multiple images by locking the emitter and collimator in place, placing the exposure shield in the first position, locking the detector in a first position and positioning the patient. The technician may then activate the x-ray emitter to capture the first image. The technician may then reposition the exposure shield to the second position, and unlock and move the detector along the guides to the second position and relock the detector in the second position all without intentionally moving the emitter, collimator, or patient. And the technician may then capture the second image.

DETAILED DESCRIPTION OF EMBODIMENTS

Figure 1:
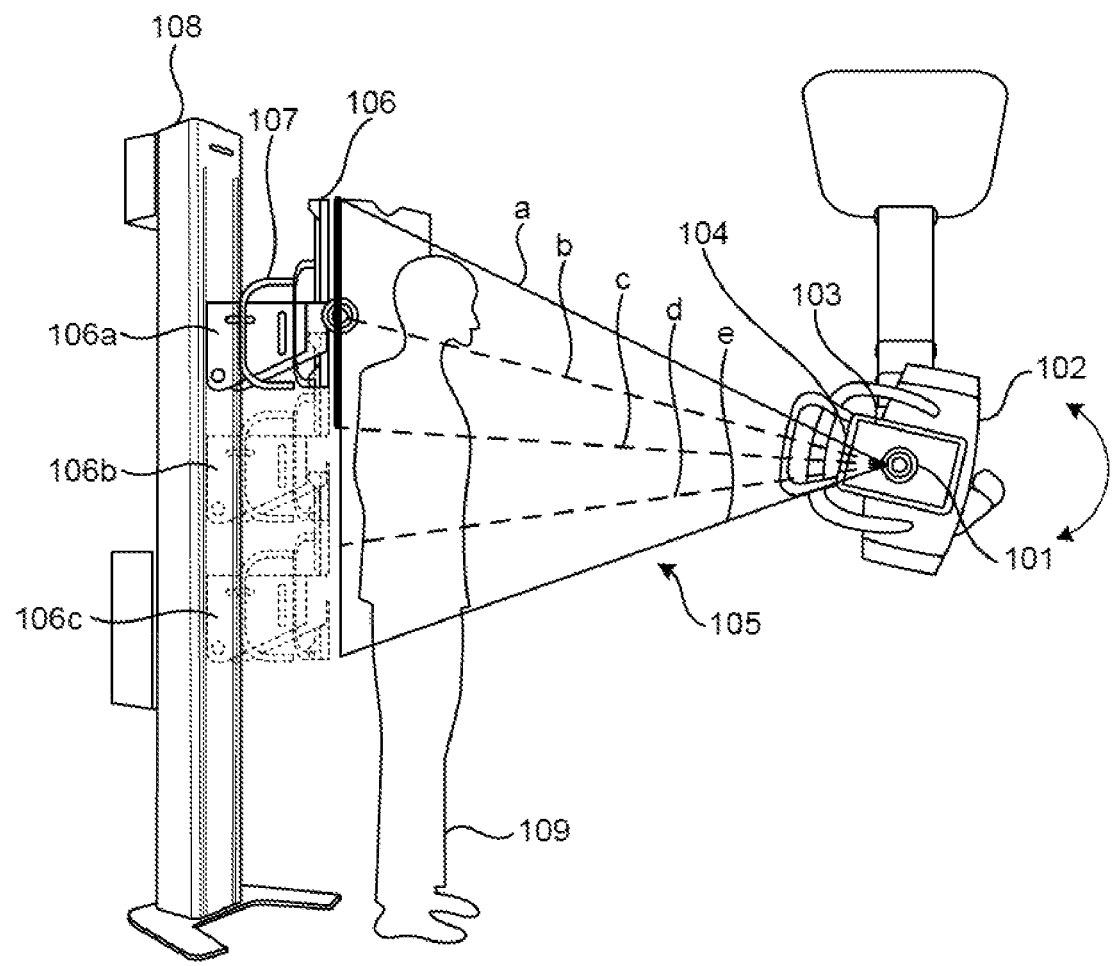
FIG. 1 is a depiction of a prior art system showing the movement of the collimator and emitter housing along with the movement of the detector.

FIG. 1 depicts the prior art system for capturing multiple images. A typical imaging facility includes a radiation emitter, such as an x-ray emitter 101 surrounded by a housing 102. The housing includes a collimator 103 having a distal end 104 that provides for the emission of x-rays (generally shown as region 105) from the housing through an aperture of the radiation emitter. The detector 106 may be mounted to a bracket 107 to allow for mobility of the detector along a structure, such as a column 108, that is likewise connected to the bracket 107.

The housing is capable of moving, for example rotating to aim the beam of x-rays emitted from the collimator at different targets. With the collimator fully open, the x-ray field emitted may be as wide as the field formed by lines a and e. However, the image detector 106, is not large enough to capture an image within the entirety of that field. Thus the collimator may be adjusted to focus the x-ray beam and the housing may be rotated such that a beam of x-rays is focused only in the field defined by lines a and c when the detector is in position 106a. The technician may then capture an image of a portion of the patient 109.

To capture a second image, the detector is moved to position 106b, the housing and collimator are rotated down and the collimator beam is refocused to capture the field area defined by lines b and d. To capture a third image, the detector is moved to position 106c, the housing and collimator are rotated down and the collimator beam is refocused to capture the field area defined by lines c and e. After all three images are captured, a technician must attempt to stitch the images together to form a single image. If, during any one of the movements described, the patient moved, or the detector was not positioned with sufficient overlap of the beam fields, or the collimator was not focused properly to ensure overlap of the beam fields, the images captured will not properly align and the technician will not be able to appropriately stich the images together.

Figure 2:
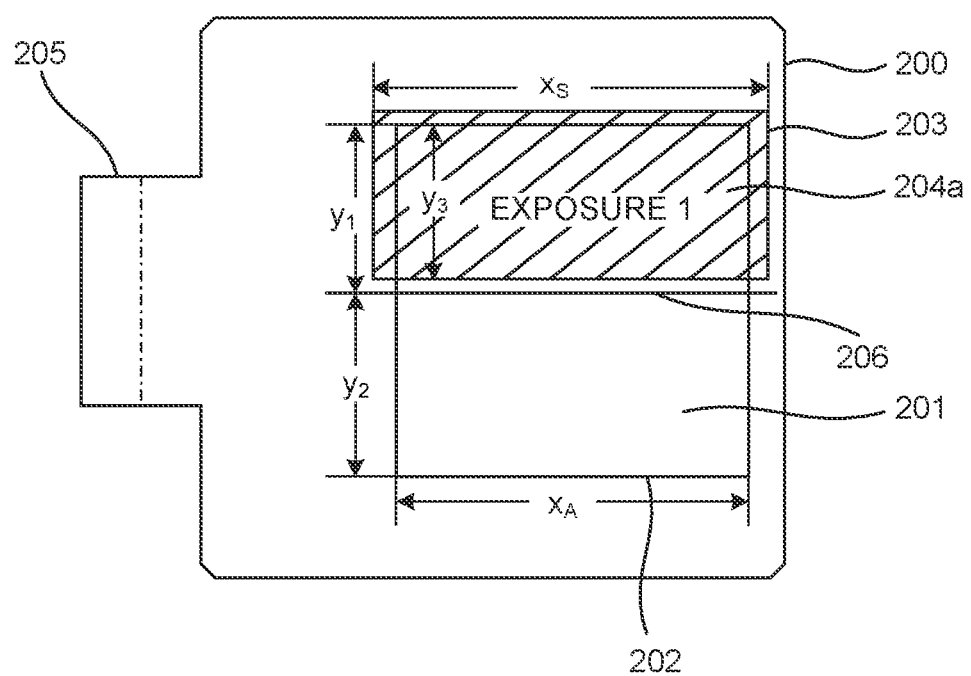
FIG. 2 is a depiction of an embodiment of an exposure shield in a first position.

FIG. 2 is a depiction of an embodiment of an exposure shield in a first position. The exposure shield includes a frame 200. The frame may be made of any suitable ridged material. In one embodiment, the frame is metal, such as aluminum. In another it is plastic, such as ABS or polypropylene. The exposure shield includes an aperture, generally indicated by numeral 201, defined by an aperture border 202 having a length and a width. The aperture allows x-rays to pass unimpeded through the frame. Generally the aperture is large enough such that when the frame is placed over a fully open collimator, it would allow substantially all x-rays emitted from the collimator to pass through it.

A typical x-ray emitter housing includes retention brackets. The brackets may be slides, pins, clips, binders or other retention mechanisms for holding an object at or near the distal end of the collimator. One embodiment of an x-ray emitter includes a bracket affixed to an upper portion of the housing, above the distal end of the collimator, and having a longitudinal groove that spans the outlet of the housing. The x-ray emitter includes a second bracket affixed to a lower portion of the housing, below the distal end of the collimator, and having a longitudinal groove that spans the outlet housing. One embodiment of the frame 200 is adapted to slide within the grooves of the brackets so as to be held by the brackets such that the aperture of the frame is positioned in-line with the outlet.

Figure 3:
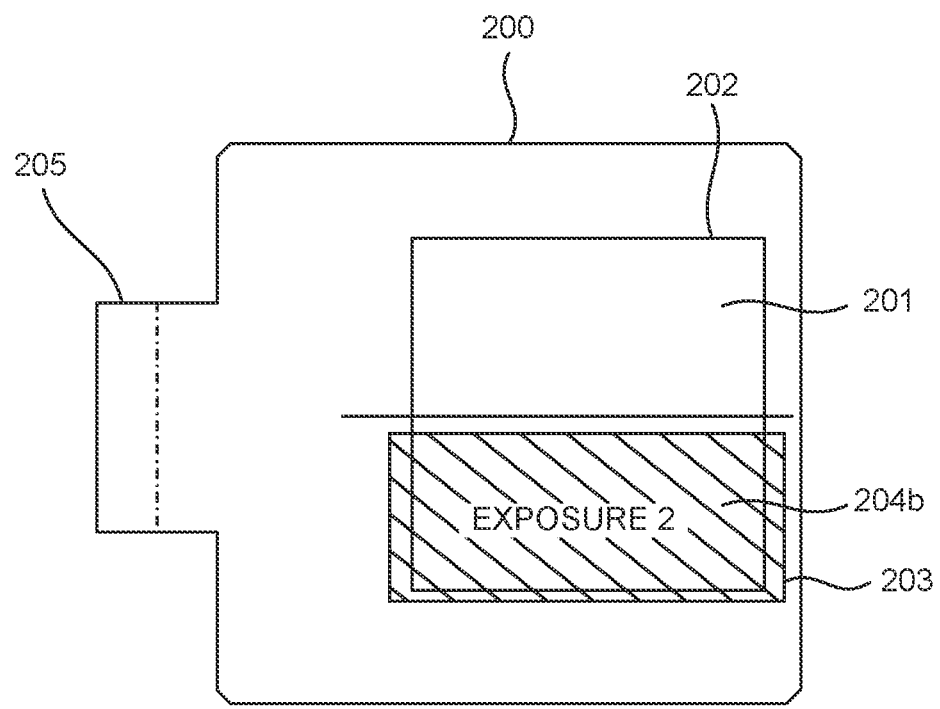
FIG. 3 is a depiction of an embodiment of an exposure shield in a second position.

In the embodiment depicted in FIG. 2 and FIG. 3, the frame is provided with a single shield 203. The shield is formed of a dense, x-ray absorbent material. Suitable materials include lead and tungsten, though others could be used. For example, it was found that to be effective the shield could provide an absorption factor equal to or greater than the equivalent of 0.5 mm of lead which has been proven in lead apron studies to absorb 96-99% of x-ray in the diagnostic range. The shield covers a portion of the aperture. In one embodiment, the shield is permanently fixed in position. For example, the shield may be fastened to the frame using fasteners, such as screws or rivets, or may be adhered to the frame. In one embodiment, the shield is integrated with the frame, for example, the entire frame and shield could be a single unitary piece of tungsten, and in such an embodiment the full "aperture"—which is the area that would allow for substantially all x-rays to pass through the frame—would be partially covered or filled in by the integrated shield. In an alternate embodiment, the shield is movably engaged with the frame. For example, the shield may include a grove about its perimeter that engages with the frame, such as by frictional engagement with aperture border, and allows the shield to be slid up and down within the aperture.

Figure 2A:
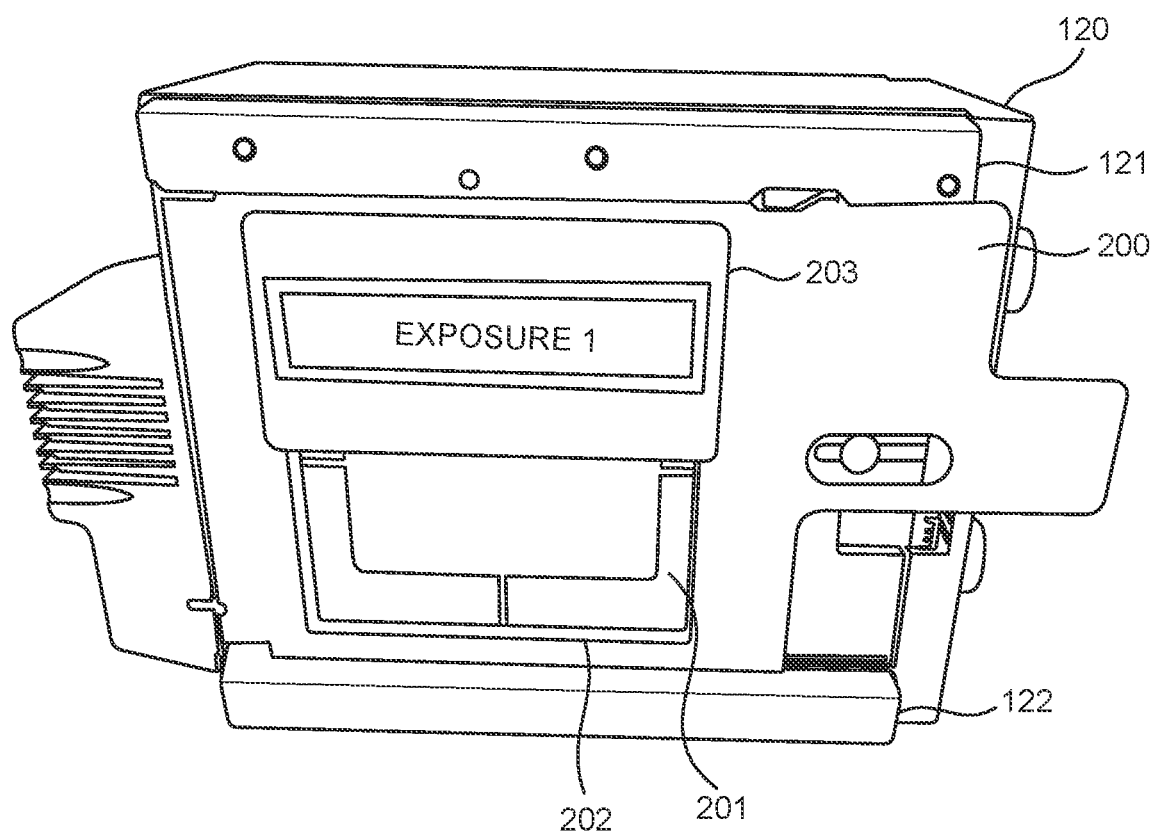
FIG. 2A is a depiction of an embodiment of an exposure shield positioned in a first position on an emitter housing at the distal end of a collimator.
Figure 3A:
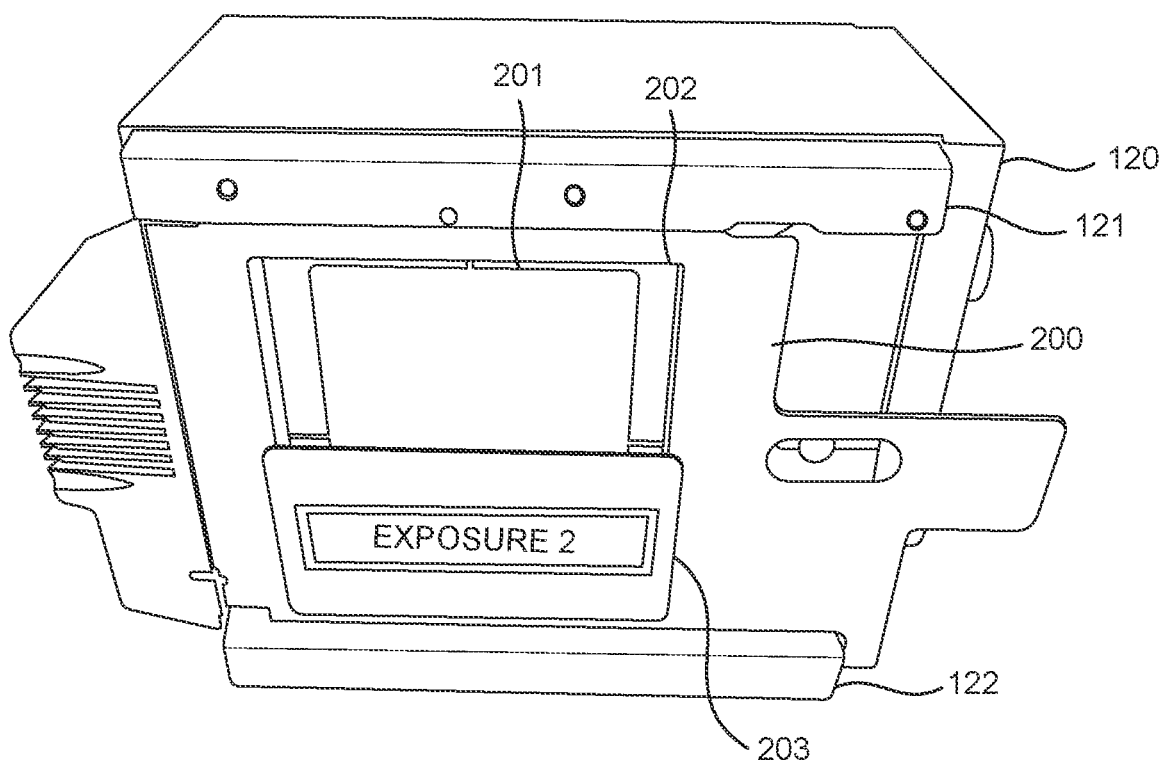
FIG. 3A is a depiction of an embodiment of an exposure shield positioned in a second position on an emitter housing at the distal end of a collimator.

In the embodiment depicted in FIGS. 2 and 3, the shield is fixed. In FIG. 2, the frame 200 is in a first position and side 204a of shield 203 is visible. In FIG. 3, the frame 200 has been flipped about its horizontal axis such that side 204b of shield 203 is visible. FIGS. 2A and 3A depict embodiments the exposure shield in orientations from FIGS. 2 and 3, respectively, held by the housing of an x-ray emitter. The emitter housing 120 includes retention brackets 121 and 122. The frame 200 slides within groves of the retention brackets and is held by the retention brackets. In one embodiment, the frame may include one or more additional tabs on one or more sides. The tab(s) may prevent the frame from connecting with the housing in the wrong position and may facilitate placement and removal of the frame from the emitter housing. In such embodiments, the frame may only be held by the retention brackets in two orientations, namely the orientation of FIG. 2 and the orientation of FIG. 3. The frame may also include a grip 205 (oriented on the left side in FIG. 2, for example, and, in an alternate embodiment, oriented on the right as in FIG. 2A, for example) to assist in attaching and removing the frame from the emitter. As shown in the FIG. 2A embodiment, the grip may overhand the housing of the emitter to provide and easily graspable portion of the frame.

The shield has particular dimensions. In the embodiment depicted in FIGS. 2 and 3, line 206 indicates an imaginary center line such that the distances $y_1$ and $y_2$ are equal and make up the length of the aperture. The aperture width is $x_A$. The distance $y_3$ (the shield length), which extends from the aperture border to the border of the shield is less than $y_1$. The shield width is $x_S$. By ensuring that $y_3$ is less than $y_1$, an image of a patient captured with the shield in the orientation shown in FIG. 2 and a subsequent image of a patient captured with the shield in the orientation of FIG. 3 are guaranteed to have a portion of each image overlap. In one embodiment, side 204a, which for reference purposes could be considered the front side, includes indicia, such as the phrase "EXPOSURE 1" and side 204b, which for reference purposes could be considered the back side, includes different indicia, such as the phrase "EXPOSURE 2." The frame may be slid into the emitter bracket with EXPOSURE 1 facing the patient and a first image may be captured. The frame may then be removed from the emitter brackets and flipped along a single axis to orient the shield in the correct second position. The frame is reinserted into the emitter brackets with EXPOSURE 2 facing the patient and a second image may be captured.

Figure 4:
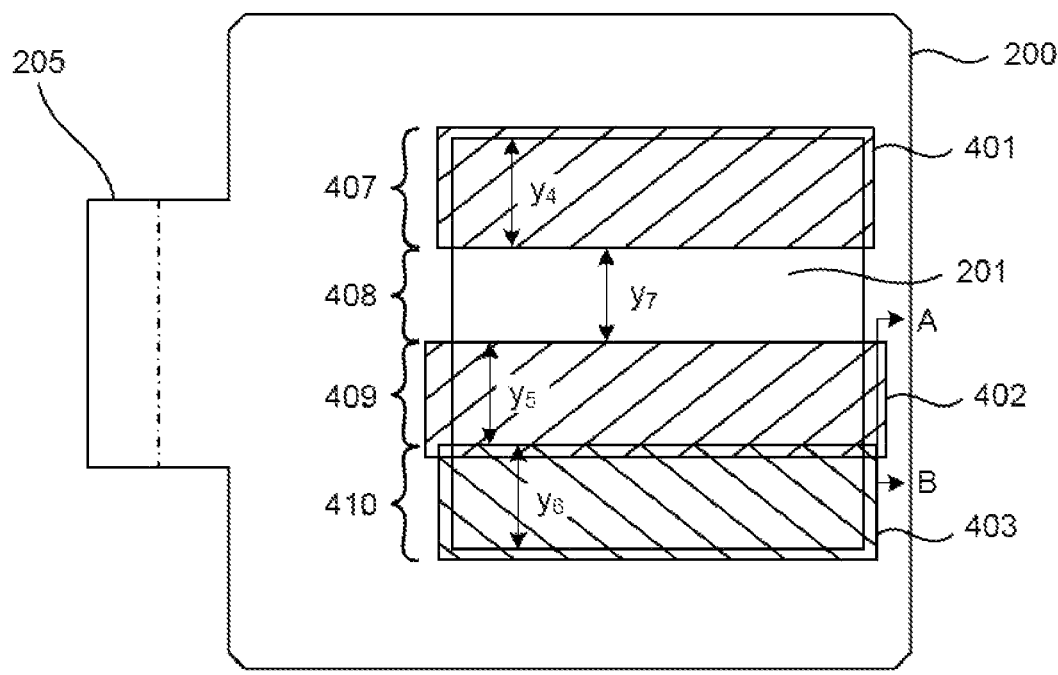
FIG. 4 is a depiction of an embodiment of an exposure shield that may be utilized to capture three or more different images.

Additional embodiments may include more than one shield. While any number of shields could be used, in typical practice anywhere from 1 to 5 shields are sufficient to capture all of the images of a typical human patient. An exemplary embodiment with three shields, 401, 402, and 403 is shown in FIG. 4, with a cross-section of shield 402 shown in FIG. 4A.

Figure 4A:
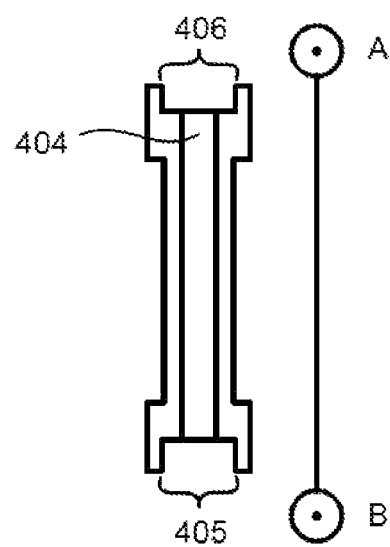
FIG. 4A is a cross-sectional view of and embodiment of a sliding shield taken along cross-sectional line AB.

The shields include a groove about their perimeters to frictionally engage the aperture border. In the embodiment of FIG. 4, shields 401 and 403 only includes grooves on three sides that engage with the aperture boarder. Shield 402 includes grooves on either vertical side that correspond to the aperture boarder and groves on either horizontal side that correspond to shields 401 and 403 respectively. As shown in FIG. 4A, groove 404 mates with the aperture border, while groove 405 mates with shield 403 while groove 406 mates with shield 401. Thus, the shields and the frame nest in a tongue-and-groove manner. It should be appreciated that while in the embodiment shown, shields 403 and 401 nest partially within a groove of shield 402, shield 402 could alternated nest partially within shield 401 or 403. Importantly, however, when placed proximate to one another, at least a portion of each shield overlaps with the other shields. In that way, gaps between the shields are eliminates so as to prevent x-rays from passing between adjacent shields. The shields may each have the same or different horizontal widths so long as the width of each is sufficient to span the entirety of the aperture. In an alternate embodiment, the aperture may include a grove in its boarder and the shields may nest and slide within the groove.

The shields may slide within the aperture. For example, in the embodiment of FIG. 4, shield 401 may slide to occupy position 407 (as shown) or position 408. Shield 402 may slide to occupy position 408 or position 409 (as shown). Shield 403 may slide to occupy position 409 or 410 (as shown).

The vertical length of the portion of the aperture that each shield blocks is less than the vertical length of the portion of the aperture though which x-rays may pass unimpeded. That is, $y_4$, $y_5$, and $y_6$ are each less than $y_7$. That ensures that there is overlap between images taken when the shield are slid between their various positions.

It should be appreciated that the vertical length of the portion of the aperture that each shield blocks may be slightly less than $[1/(N+1)]*L$ where N is the number of shields and L is the vertical length of the aperture (for example the length $y_1+y_2$ in FIG. 2). Thus, the vertical length of the portion of the aperture that the shield of FIG. 2 blocks (i.e. $y_3$) is slightly less than ½ of the aperture length while the vertical length of the portion of the aperture that shields 401, 402, and 403 block ($y_4$, $y_5$, $y_6$) is slightly less than ¼ the aperture length. It should be understood that embodiments of the apparatus described herein may be scaled such that the perimeter of the aperture boarder is substantially equal to the perimeter of the emitter outlet.

Once again, by blocking a portion of the aperture such that the portion of the aperture that allows x-rays to pass unimpeded is larger than the portion of the aperture that any one shield block ensures that there will be overlap between subsequently captured images. The overlap may then be matched to stitch the images together. It was found that shields having vertical lengths that are approximately 0.05%-5% less than $[1/(N+1)]*L$ are able to provide sufficient overlap between images. While over 5% could be utilized, going over that amount risks unnecessarily dosing the patient with more radiation than is necessary to achieve images that may be appropriately stitched.

Figure 5B:
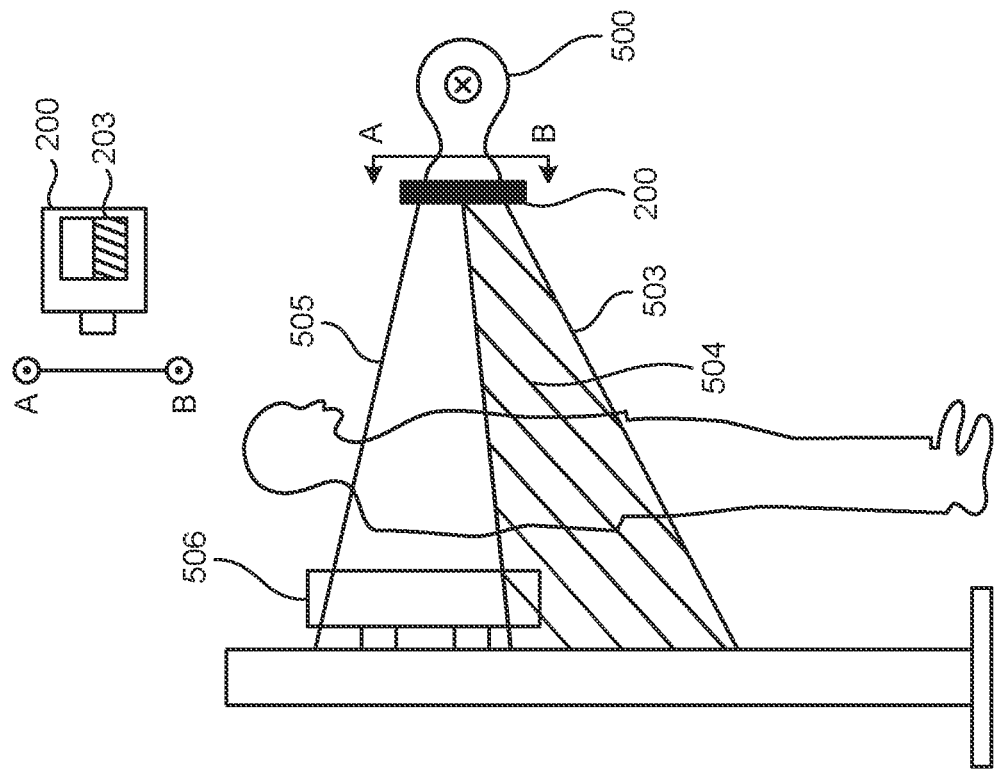
FIG. 5B is a depiction of an embodiment of present system showing the field of x-ray exposure when utilizing an embodiment of the exposure shield in a second position with an image of the shield on the collimator in a second position.
Figure 5A:
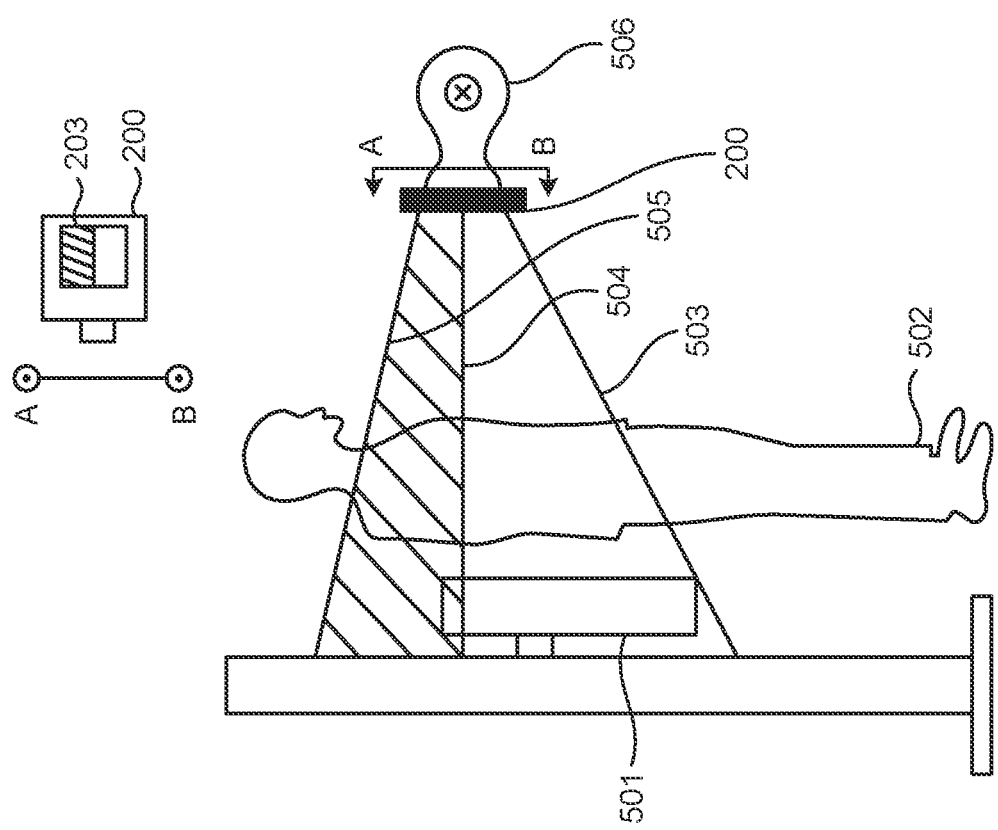
FIG. 5A is a depiction of an embodiment of present system showing the field of x-ray exposure when utilizing an embodiment of the exposure shield in a first position along with an image of the shield on the collimator in a first position.

FIGS. 5A and 5B provide a depiction of the system in operation. Frame 200 having shield 203 is affixed to the outlet of emitter housing 500. The collimator (not shown) within the emitter housing is fully opened. Detector 501 is positioned to capture x-rays and a patient 502 is positioned between the emitter housing and the detector. X-rays are emitted from the emitter though the collimator and the shield blocks slightly less than half of the whole emitting field that could be projected by the collimator (defined by lines 505 and 503) such that x-rays are only emitted in the field defined by lines 504 and 503 (note, the lines are exaggerated for exemplary purposes and are not drawn to scale). The detector may then be moved to the position 506, and the frame 200 is flipped vertically and affixed to the emitting end of the emitter housing 500. X-rays are emitted from the emitter though the collimator and the shield blocks slightly less than half of the whole emitting field that could be projected by the collimator (defined by lines 505 and 503) such that x-rays are only emitted in the field defined by lines 505 and 504. The collimator and x-ray emitter are both unmoved in the process.

A further embodiment matches a detector cabinet including a detector with the shield apparatus. It should be understood that while the detector cabinet is referred to as a cabinet, it need not be a fully enclosed structure.

Figure 6:
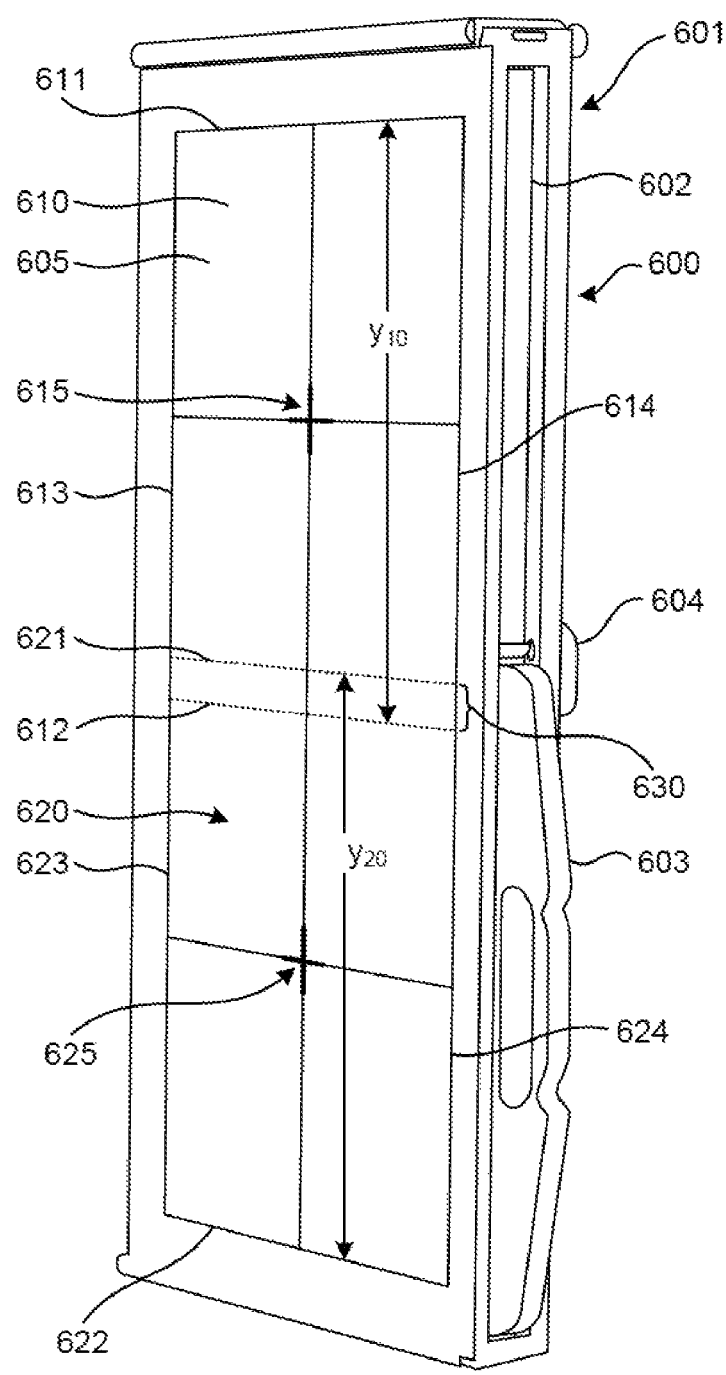
FIG. 6 is a depiction of an embodiment of a detector and detector cabinet that matches with an embodiment of an exposure shield.
Figure 6B:
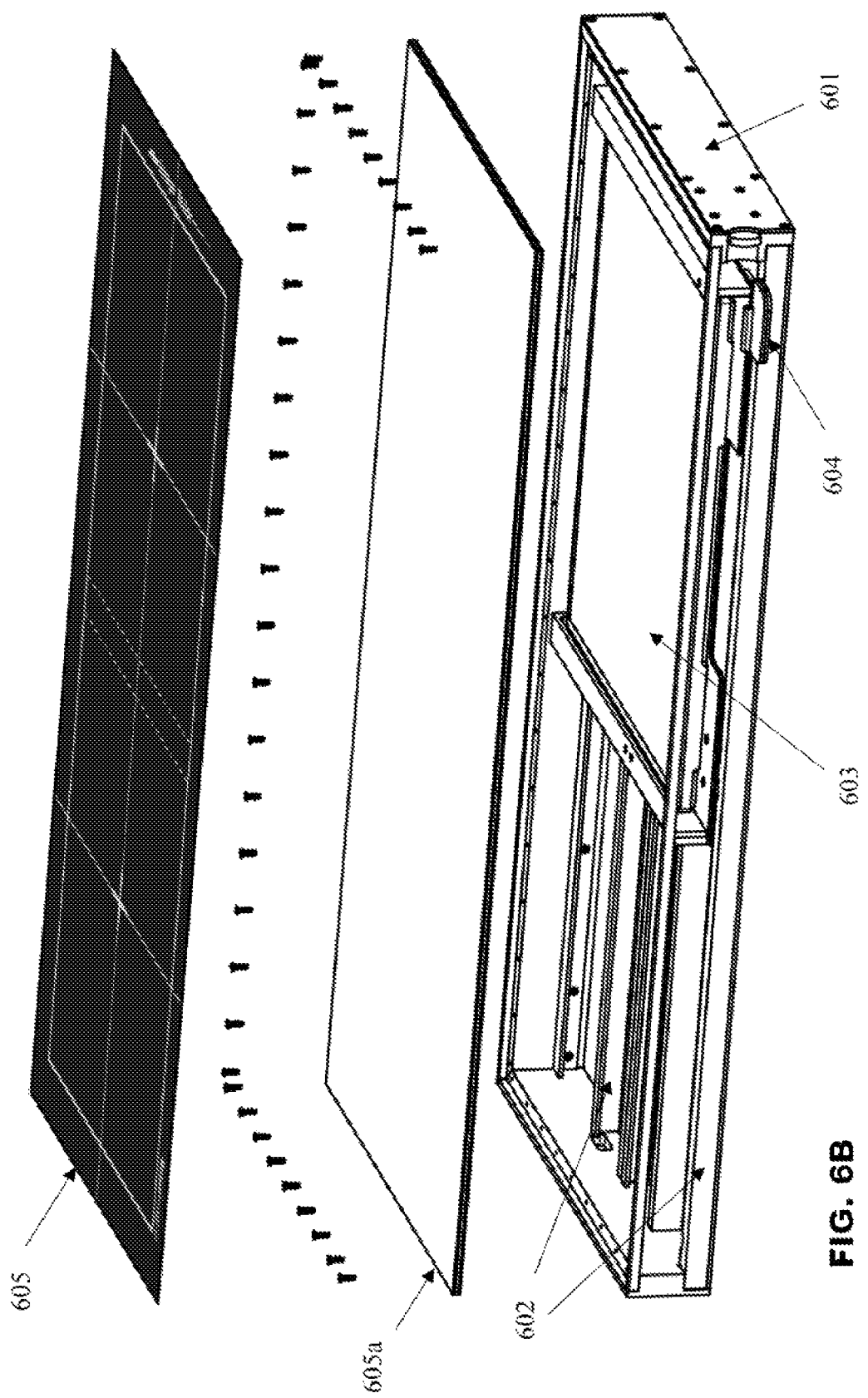
FIG. 6B is an exploded view of an embodiment of a detector and detector cabinet that matches with an embodiment of an exposure shield.

FIGS. 6A and 6B depict an embodiment of detector cabinet 600. FIG. 6B is an exploded view. The cabinet includes a cabinet frame 601 having one or more guides 602. The cabinet frame houses the detector 603 such that the detector may be moved along the one or more guides. The detector further is adapted to engage the frame such that it may be held fast in multiple positions. For example, the detector or cabinet may include lock that engages to lock the detector and the cabinet frame together. In the embodiment of FIG. 6A, the detector includes a lock 604 that engages and disengages the guide 602 to hold the detector in a desired position or allows the detector to be slid along the guide 602, respectively.

The cabinet includes a static front face 605 that covers the detector as the detector is moved and held in multiple positions. The front face includes indicia that is matched with an exposure shield. For example, the front face 605 includes indicia that is matched with the exposure shield of FIGS. 2 and 3. As shown in FIG. 6B, the front face 605 may be a sheet, such as a plastic laminate, that may be attached to a support base 605*a*. That way, if the indicia on the front face is damaged, it can be easily replaced. Alternatively, the front face could be integrated with the support base or painted on the support base. The front face and support base may be attached to the cabinet frame by fasteners, such as screws or bolts for example. The indicia includes an upper zone 610, defined by upper zone top line 611, upper zone side lines 613 and 614, and upper zone dashed bottom line 612. The indicia includes an lower zone 620, defined by lower zone dashed top line 621, lower zone side lines 623 and 624, and lower zone bottom line 622. Upper zone 610 includes center target 615 and lower zone 620 includes a center target 625. The center targets correspond to the desired center point for the field of x-rays that pass through the unshielded portion of the aperture 201 when the shield apparatus of FIGS. 2 and 3 is applied to the emitter housing. For example, when the shield apparatus is applied in the position of FIG. 2 for Exposure 1, the center target of the x-rays emitted through the unshielded portion of aperture 201 is center target 625. For example, when the shield apparatus is applied in the position of FIG. 3 for Exposure 2, the center target of the x-rays emitted through the unshielded portion of aperture 201 is center target 615.

The indicia define the outline of upper zone 610 having a length of $y_{10}$, and define the outline of lower zone 620 having a length of $y_{20}$. In the embodiment of FIG. 6, $y_{10}$ and $y_{20}$ are essentially equal. The length of the detector 603 is at least as long as $y_{10}$ and $y_{20}$ and may be slightly longer. It has been found that a detector that is approximately 1%-5% longer than $y_{10}$ and $y_{20}$ is sufficient.

With the foregoing configuration, the dashed lines 612 and 622 form an overlap zone 630, and when the detector is moved from its upper most position to its lower most position, at least a portion of the detector is guaranteed to remain covered by the overlap zone. The overlap zone 630 corresponds to the portion of the aperture 201 of the shield apparatus of FIGS. 2 and 3 that is never blocked regardless of whether the shield apparatus is positioned as in FIG. 2 or positioned as in FIG. 3. That results in images having overlap corresponding to the overlap zone which facilitates alignment of the images for stitching. It should be understood that alternate indicia could be applied to the front face to create upper, lower, and middle zones with multiple overlap zones that correspond to embodiments having multiple shields, such as the embodiment of FIG. 4.

Figure 7:
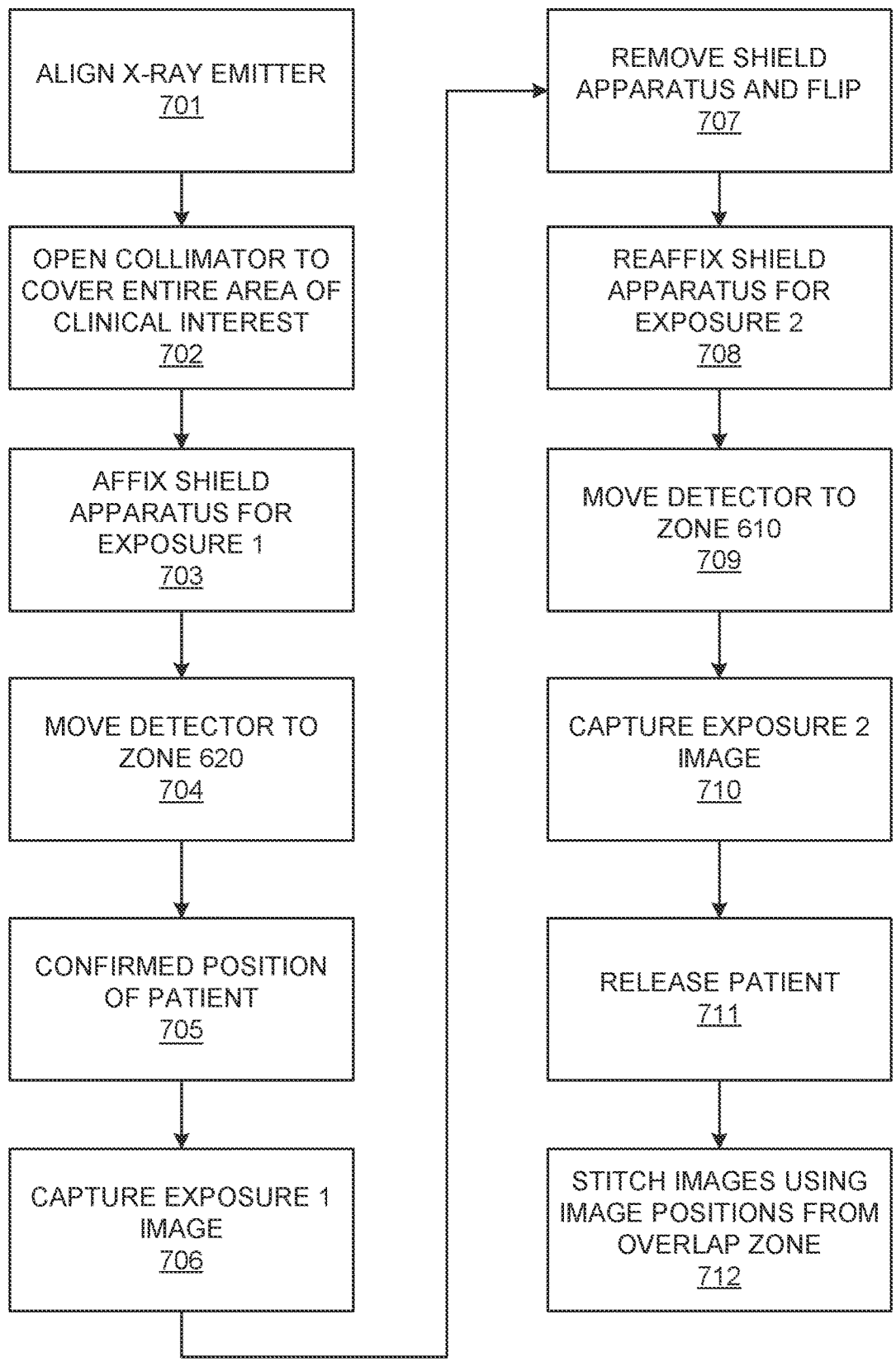
FIG. 7 is a flowchart setting forth a progression of utilization of the exposure shield and cabinet.

FIG. 7 is a flow chart that sets forth an exemplary method of utilizing the shield apparatus and a detector. First, the technician aligns the x-ray emitter parallel to the ground to provide the widest/tallest possible field of x-ray emission at 701. The technician also opens the collimator to cover the entire area of clinical interest with x-ray emissions at 702. The technician affixes the shield apparatus to the housing with "EXPOSURE 1" right-side up and facing outward at 703. The technician moves the detector such that it is covered by zone 620 at 704. The patient is positioned in the proper posture is confirmed at 705. The technician the takes the image of EXPOSURE 1 at 706. Without intentionally moving the emitter or the collimator, the technician removes that shield apparatus and flips it along the horizontal axis at 707. Without intentionally moving the emitter or collimator, the technician then reaffixes the shield apparatus to the housing with "EXPOSURE 2" right-side up and facing outwards at 708. The technician moves the detector to such that it is covered by zone 610 at 709. The technician takes the image of EXPOSURE 2 at 710. The patient may then be released from the hold position at 711. The technician or another may then stitch together the images of the two exposures using the portions of the images that were captured in the overlap zone 630 at 712.

Although the present apparatus and system has been described in terms of various embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A method of capturing multiple x-ray images comprising:
    positioning an x-ray detector in a first position sufficient to capture a first clinical region of interest, the x-ray detector comprising an area adapted to detect x-rays;
    positioning or adjusting an emitter or collimator within a housing such that, if activated, the emitter would emit x-rays from the housing over an area that is either a) greater than the first clinical region of interest; or b) greater than the area of the x-ray detector adapted to detect x-rays; and
    then, coupling to the exterior of the housing a frame having an aperture with an aperture length and an aperture width, at least one shield having a shield length and a shield width; the at least one shield being positioned within the aperture; and wherein the shield width is greater than or equal to the aperture width and the shield length is less than half the aperture length; and
    then, emitting x-rays from the housing for a first period of time, and
    then, moving the x-ray detector to a second position sufficient to capture a second clinical region of interests;
    uncoupling the frame from the housing, inverting the frame, and recoupling the inverted frame to the housing; and
    then emitting x-rays from the housing for a second period of time.

2. The method of capturing multiple x-ray images of claim 1 wherein uncoupling the frame from the housing, inverting the frame, and recoupling the inverted frame to the housing is accomplished without intentionally adjusting either the collimator or the emitter.

3. The method of capturing multiple x-ray images of claim 1 wherein, when the x-ray detector is in the second position, a portion of the area of the x-ray detector adapted to detect x-rays overlaps a portion of the area that the x-ray detector occupied when the x-ray detector was in the first position.

4. The method of capturing multiple x-ray images of claim 3 further comprising: after emitting x-rays from the housing for a second period of time, utilizing the overlapping portion detected by the detector to align an image corresponding to the first position and an image corresponding to the second position.

5. A method of capturing multiple x-ray images comprising:
    positioning an x-ray detector in a first position sufficient to capture a first clinical region of interest, the x-ray detector comprising an area adapted to detect x-rays;
    positioning or adjusting an emitter or collimator within a housing such that, if activated, the emitter would emit x-rays from the housing over an area that is either a) greater than the first clinical region of interest; or b) greater than the area of the x-ray detector adapted to detect x-rays; and
    then, coupling to the exterior of the housing a frame having at least one shield having a shield length and a shield width; wherein the shield length and width are together sufficient to block a first x-ray field that comprises at least and no more than 45% to 49.5% of the x-rays to be emitted from the housing when the frame is coupled to the exterior of the housing; and
    then, emitting x-rays from the housing for a first period of time, and
    then, moving the x-ray detector to a second position sufficient to capture a second clinical region of interests;
    moving the at least one shield to a second position such that the shield length and width are together sufficient to block a second x-ray field that does not overlap the first x-ray field;
    ensuring that the frame is coupled to the exterior of the housing when the shield is in the second position; and
    then emitting x-rays from the housing for a second period of time.

6. The method of capturing multiple x-ray images of claim 5 wherein uncoupling the frame from the housing, inverting the frame, and recoupling the inverted frame to the housing is accomplished without intentionally adjusting either the collimator or the emitter.

7. The method of capturing multiple x-ray images of claim 5 wherein, when the x-ray detector is in the second position, a portion of the area of the x-ray detector adapted to detect x-rays overlaps a portion of the area that the x-ray detector occupied when the x-ray detector was in the first position.

8. The method of capturing multiple x-ray images of claim 7 further comprising: after emitting x-rays from the housing for a second period of time, utilizing the overlapping portion detected by the detector to align an image corresponding to the first position and an image corresponding to the second position.

9. A method of capturing an x-ray image comprising:
    arranging proximal to one another an x-ray detector and a housing, the housing a) having associated with it at least one retention bracket, and b) containing an x-ray emitter and adjustable collimator;
    arranging between the x-ray detector and the housing a subject having a clinical area of interest comprised of a first half and a second half;
    adjusting the collimator such that it is arranged to focus x-rays emitted from the housing over the entire clinical area of interest;
    using the retention bracket, coupling a frame having a shield to the housing in a first orientation such that the shield is positioned to block a portion of the second half of the clinical area of interest but less than the entire second half of the clinical area of interest from being intentionally exposed to x-rays;

ensuring that the x-ray detector is positioned such that it is adapted to detect x-rays passing through the first half of the clinical area of interest; and emitting x-rays from the housing such that a portion of the x-rays are blocked by the shield and such that the subject and the x-ray detector are exposed to a portion of the x-rays in the entire first half of the area of clinical interest and in only in a first portion of the second half of the area of clinical interest.

10. A method of capturing an x-ray image as in claim 9 further comprising:

without adjusting the subject, the x-ray emitter, or the collimator, moving the frame and shield and, using the retention bracket, coupling the frame and shield to the housing in a second orientation such that the shield is positioned to block a portion of the first half of the clinical area of interest but less than the entire first half of the clinical area of interest from being intentionally exposed to x-rays;

ensuring that the x-ray detector is positioned such that it is adapted to detect x-rays passing through the entire second half of the clinical area of interest as well as a first portion of the first half of the clinical area of interests; and emitting x-rays from the housing such that a portion of the x-rays are blocked by the shield and the subject and the x-ray detector are exposed to a portion of the x-rays in the entire second half of the area of clinical interest and in only a portion of the first half of the area of clinical interest; and wherein the portion of the second half of the clinical area of interest exposed to x-rays in the first exposure and the portion of the first half of the clinical area of interest exposed in the second exposure overlap.

11. A method of capturing an x-ray image as in claim 10 further comprising:

creating two images based on the x-rays detected by the detector during the first and second exposures;

overlapping the first image with the second image so as to match the portion of the second half of the clinical area of interest exposed to x-rays in the first exposure and the portion of the first half of the clinical area of interest exposed in the second exposure overlap;

forming a single composite image from the two images.

* * * * *